United States Patent
Sudkamp et al.

(10) Patent No.: US 11,482,044 B2
(45) Date of Patent: Oct. 25, 2022

(54) METHOD FOR PHOTOCOPYING A SEQUENCE OF CUT SURFACES INSIDE A LIGHT-SCATTERING OBJECT WITH IMPROVED SCANNING

(71) Applicant: Visotec GmbH, Lubeck (DE)

(72) Inventors: Helge Sudkamp, Lubeck (DE); Hendrik Spahr, Lubeck (DE); Dierck Hillmann, Lubeck (DE); Peter Koch, Lubeck (DE); Gereon Huttmann, Lubeck (DE)

(73) Assignee: Visotec GmbH, Lubeck (DE)

( * ) Notice: Subject to any disclaimer, the term of this patent is extended or adjusted under 35 U.S.C. 154(b) by 93 days.

(21) Appl. No.: 16/981,756

(22) PCT Filed: Feb. 5, 2019

(86) PCT No.: PCT/EP2019/052765
§ 371 (c)(1),
(2) Date: Sep. 17, 2020

(87) PCT Pub. No.: WO2019/179687
PCT Pub. Date: Sep. 26, 2019

(65) Prior Publication Data
US 2021/0034863 A1    Feb. 4, 2021

(30) Foreign Application Priority Data
Mar. 19, 2018  (DE) .................. 10 2018 106 292.3

(51) Int. Cl.
*G06V 40/19*    (2022.01)
*A61B 3/10*    (2006.01)
(Continued)

(52) U.S. Cl.
CPC .............. *G06V 40/19* (2022.01); *A61B 3/102* (2013.01); *A61B 3/12* (2013.01); *A61B 3/14* (2013.01);
(Continued)

(58) Field of Classification Search
None
See application file for complete search history.

(56) References Cited

U.S. PATENT DOCUMENTS 6,485,413 B1 * 11/2002 Boppart .................. A61B 1/07
600/478
10,430,644 B2 * 10/2019 Mathieu ............... G06V 10/141
(Continued)

FOREIGN PATENT DOCUMENTS

EP        2565725 A1    3/2013
WO    2010092533 A1    8/2010

OTHER PUBLICATIONS

International Search Report dated Mar. 29, 2019.
(Continued)

*Primary Examiner* — Chikaodili E Anyikire
(74) *Attorney, Agent, or Firm* — Wood, Phillips, Katz, Clark & Mortimer

(57) ABSTRACT

The invention relates to a free-beam interferometric method for illuminating a sequence of sectional areas in the interior of the light-scattering object. The method makes it possible for the user to select a larger image field and/or a higher image resolution than previously possible with the occurrence of self-interference of the specimen light from a scattering specimen.

6 Claims, 1 Drawing Sheet

(51) Int. Cl.
*A61B 3/12* (2006.01)
*A61B 3/14* (2006.01)
*G01B 9/02* (2022.01)
*G01B 9/02091* (2022.01)
*G03H 1/00* (2006.01)
*G03H 1/04* (2006.01)
*G06V 10/145* (2022.01)

(52) U.S. Cl.
CPC ..... *G01B 9/02047* (2013.01); *G01B 9/02084* (2013.01); *G01B 9/02091* (2013.01); *G03H 1/0011* (2013.01); *G03H 1/0443* (2013.01); *G03H 1/0465* (2013.01); *G06V 10/145* (2022.01); *G03H 2001/0033* (2013.01); *G03H 2001/0456* (2013.01); *G03H 2001/0467* (2013.01); *G03H 2210/33* (2013.01); *G03H 2222/24* (2013.01)

(56) References Cited

U.S. PATENT DOCUMENTS

2013/0057935 A1* 3/2013 Joo .................... G03H 1/16 359/10
2016/0252880 A1 9/2016 Sánchez Ortiga et al.
2018/0156597 A1* 6/2018 Smith ................ G01B 9/02067
2019/0365220 A1* 12/2019 Frisken .................... G06T 7/33

OTHER PUBLICATIONS

Pavillon N et al. "Iterative method for zero-order suppression in off-axis digital holography" Optics Express, OSA Publishing, US, vol. 18. No. 15. Jul. 19, 2010 (Jul. 19, 2010). pp. 15318-15331.

Pavillon N et al. "Suppression of the zero-order term in off-axis digital holography through nonlinear filtering" Applied Optics, Optical Society of America, Washington, DC; US, vol. 48, No. 34, Nov. 9, 2009 (Nov. 9, 2009), pp. HI 86-HI 95.

Helge Sudkamp et al. "In-vivo retinal imaging with off-axis full-field time-domain optical coherence tomography" Optics Letters, US, vol. 41, No. 21, Oct. 25, 2016 (Oct. 25, 2016), p. 4987.

Helge Sudkamp et al. "Simple approach for aberration-corrected OCT imaging of the human retina" Optics Letters, US, vol. 43, No. 17, Aug. 27, 2018 (Aug. 27, 2018), p. 4224.

* cited by examiner

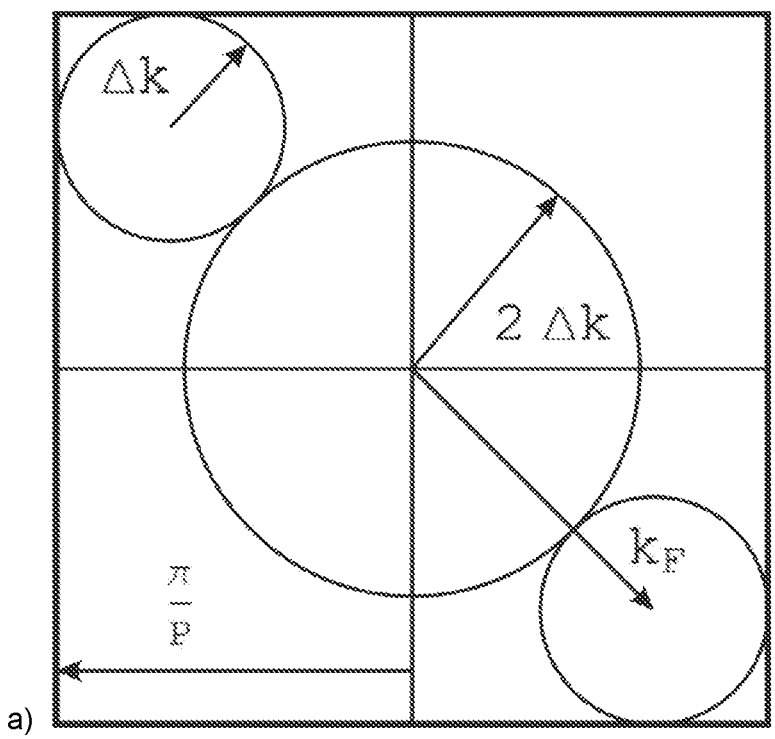
a)
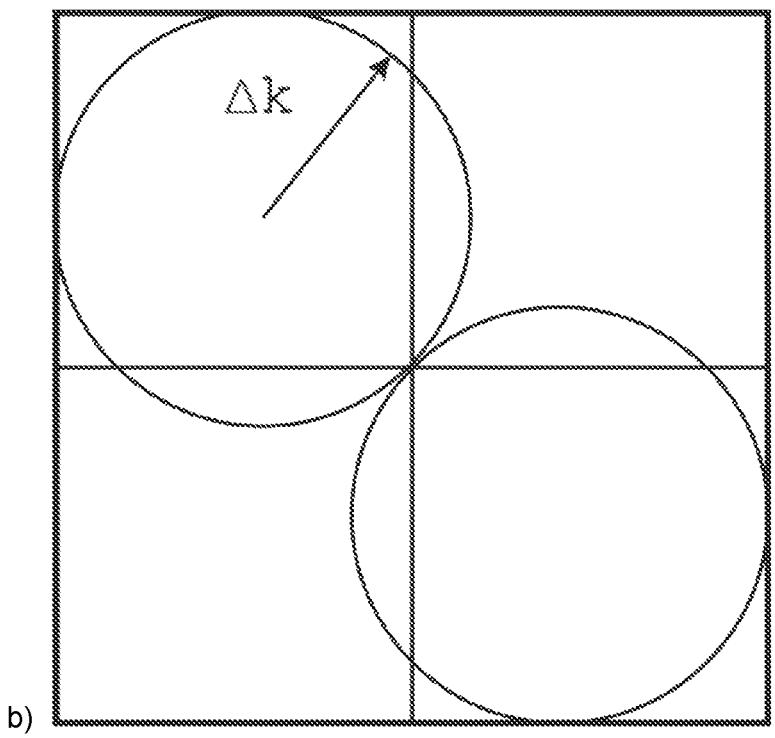
b)

METHOD FOR PHOTOCOPYING A SEQUENCE OF CUT SURFACES INSIDE A LIGHT-SCATTERING OBJECT WITH IMPROVED SCANNING

BACKGROUND OF THE INVENTION

Field of the Invention

The invention relates to a method for illuminating sectional areas in the interior of a light-scattering object, wherein light of a short-coherent light source is split into a specimen light beam and a reference light beam and fed to a specimen arm and a reference arm variable in its length and thereafter superimposed on a two-dimensional light detector.

Background Art

Interferometric methods of the generic type are known, amongst other things, for optical coherence tomography (OCT). In particular, it is possible by means of free-beam interferometers to detect simultaneously the whole of the light scattered by a two-dimensionally extending specimen ("full-field OCT, FF-OCT) and to superimpose the latter on a two-dimensional light detector—e.g. a CCD or CMOS camera—with the reference light. The two-dimensional interferograms thus generated and electronically detected contain amongst other things information concerning sectional areas in specimen interiors and can be evaluated by processing in a computer in order to extract this information.

Publication U.S. Pat. No. 7,088,454 B2 proposes for example one such FF-OCT method, in which by way of illustration legends imprinted upon one another at different depths of a test specimen are read out from the OCT measurement data. The reading depth, i.e. the specimen depth, from which the reading is taken corresponds to the length of the reference arm. For each selected reading depth, two interferograms are detected which differ in that the reference light on the one hand is phase-shifted by $\pi/2$ and on the other hand not. In addition, a background image is detected, the reference beam being faded out. The sectional images are calculated from these three images. It is also ascertained that artifacts ("random noise") can occur for example due to vibrations of the measurement structure. As a remedy, U.S. Pat. No. 7,088,454 B2 proposes detecting the interferograms repeatedly over a time period and then calculating and evaluating the temporal mean values.

Publication WO 2017/029160 A1 discloses an FF-OCT method, which creates a tilted incidence of the reference light onto the light detector, as it is otherwise known from Off-Axis Digital Holography (OA-DH). On condition of a sufficient size of the speckles of interference light on the camera—in relation to pixel pitch P different phase positions of the reference light are simultaneously detected, and the phase gradient along the camera serves at the same time to separate interference and background light by means of Fourier filtering.

In particular, the method of WO 2017/029160 A1 uses spatially partial coherent light with a short coherence length—less than 25 microns—from the NIR spectrum, and the free-beam interferometer comprises a reference arm which is variable in its length by means of a displaceable reference mirror. Its interference on the two-dimensional light detector—e.g. a CCD or CMOS camera—at the output of the interferometer occurs only when the optical path lengths of reference light and scattered specimen light coincide within the coherence length. The variable reference arm thus allows specimen light from different specimen depths to be brought into a state of interference with the reference light. The change in length of the reference arm can be carried out by the reference mirror displaceable along the optical axis in the manner of the known "time-domain" (TD) OCT, wherein a repeating movement of the mirror for repeated depth scans is possible.

The method of WO 2017/029160 A1 is, according to the aforesaid, clearly distinguished by the concept "Off-Axis Full-Field Time-Domain OCT" (OA-FF-TD-OCT) from other OCT methods.

When diffusely scattering specimens such as for example biological tissue are examined with one of the aforementioned methods, the interference of the specimen light with itself, i.e. the superimposition of light components scattered at different depths, plays a role.

The half bandwidth of the spatial frequencies of the cross-correlated interference signal—generated by the superimposition of specimen and reference light on the camera—is determined by central wavelength $\lambda_0$ and numerical aperture NA of the image of the specimen and amounts to $$\Delta k = \frac{2\pi NA}{\lambda_0}$$

The auto-correlated interference signal—due to self-interference of specimen light—has 2 $\Delta k$ as a half bandwidth, and the two signals occur simultaneously in the electronically detected interferograms. This means that the Fourier coefficients of the two signals are only substantially different from zero for wave number vectors with $|\vec{k}|<\Delta k$ for the cross-correlated and $|\vec{k}|<2\ \Delta k$ for the auto-correlated, i.e. they occur "mixed" with the Fast Fourier Transform (FFT) of the interferograms over a common definition range of the Fourier space.

Due to the tilted irradiation of the reference light, a phase gradient is established along an axis in the camera plane, which leads to a detectable interference stripe pattern (fringes). This periodic modulation with predetermined wave number vector $\vec{k}_F$ relates only to the cross-correlated and displaces all the associated Fourier coefficients with respect to those of the auto-correlated. The signals can thus be separated by Fourier filtering, when $|\vec{k}_F|\geq 3\ \Delta k$ Is established, because the definition ranges of the Fourier coefficients of the two signals are then safely disjoint.

The described procedure has the drawback that, with every actual camera with an infinite number of light-sensitive pixels, it is also necessary to move in an infinite Fourier space which is used in anything other than a favourable manner if the Fourier coefficients of the cross-correlated signal of interest are moved into an edge region of this Fourier space. Typically, not even 10% of the available Fourier space is used for the useful signal. The theoretical optimum lies at 50%, since even the complex-conjugated useful signal is unavoidably generated, which however does not deliver any additional information.

Poor utilisation of the Fourier space is equivalent to oversampling of the contribution of the cross-correlated to the interferograms. Improved scanning would permit sectional images of the specimen with increased resolution and/or enlarged image field to be achieved without increasing the measurement or computing time.

SUMMARY OF THE INVENTION

The problem of the invention, therefore, is to develop the OA-FF-TD-OCT method known per se such that an improved scanning of the cross-correlated interference signal is achieved.

The problem is solved by a method for illuminating a sequence of sectional areas in the interior of a light-scattering object with the steps:
provision of a light source, which emits light with a predetermined central wavelength $\lambda_0$ and a coherence length less than 25 microns;
splitting the light of the light source into specimen light and reference light;
illumination of the object over the surface with the specimen light;
imaging of the specimen light scattered by the object with numerical aperture NA onto an electronic camera with pixels with a pitch P along a least one axis in the camera plane;
causing interference of reference light and specimen light on the camera by establishing a path length profile and a phase gradient of the reference light along the predetermined axis in the camera plane;
displacement of the path length profile of the reference beam at a time-dependent rate; and
detection of further camera images in each case at least indexed with a dimension for the time-dependent displacement of the path length profile, wherein the condition $$\frac{\sqrt{2}}{3+\sqrt{2}}\lambda_0 < \frac{2NA*P}{M} \leq \frac{\sqrt{2}}{1+\sqrt{2}}\lambda_0$$

is met where M is the magnification factor of the image.

The sub-claims specify advantageous embodiments of the method.

It should be noted that the present invention represents a development of the invention from WO 2017/029160 A1 and develops the latter in an advantageous and non-obvious way. In the context of this description, an electronic camera with pixels with a pitch P (centre to centre) should be used.

The concept of the path length profile is taken from WO 2017/029160 A1 with the following explanation concerning the realisation of the cross-correlated signal:

Both the speckles and also the fringes of the stripe pattern only appear on the camera when reference and specimen light components on the camera pixels have the same path length and are therefore coherent. When it falls on the camera, the reference beam defines a path length profile on the pixels along the axis with the phase gradient. The imaged object points, the scattered light whereof has the same path length profile, lie on a sectional area in the interior of the scattering object. As a rule, the sectional area is a plane, the normal whereof is tilted towards the optical axis.

The path length profile on the camera depends directly on the path length distribution in the beam cross-section of the reference beam, when the latter strikes the camera plane. If the reference light is deflected by mirrors or prisms, so that it is obliquely incident, phrase fronts and pulse fronts of the light coincide, i.e. the path length is everywhere the same in the beam cross-section parallel to the phase front. A linear path length profile is however established on the camera, which for example has a path length interval with an interval breadth of approximately 500 wavelengths $\lambda_0$, i.e. typically several hundred microns. Strictly speaking, the path length profile on the camera is a function of the two pixel coordinates, but it varies here only along an axis which is predetermined by the incident plane of the reference light.

The path length profile of the reference light on the camera can be specified by the user. This profile establishes which sectional area of the object—with regard to orientation, shape and distance from the camera—can then contribute to interference in the detected camera image. In particular, the path length profile can be displaced by changing the reference arm length, i.e. changed in its entirety to smaller or greater values overall on the camera. Further sectional areas of the object thus become available to the illumination. A sequence of camera images for the different sectional images can be detected during the displacement of the path length profile. The camera images should be detected at least indexed with a dimension of the displacement of the path length profile and should usually also be stored in a non-volatile manner. The camera images can moreover carry further indexes, for example be numbered consecutively. A dimension of the displacement can be a length measurement, for example the reference arm length, or also a control signal for the actuating drive of a reference mirror.

Path length profile and phase gradient are not necessarily coupled with one another. The phase gradient depends solely on the angle of incidence of the reference beam on the camera.

BRIEF DESCRIPTION OF THE DRAWINGS

The single FIG. 1 also serves for the following explanation of the invention. In the FIGURE:

FIG. 1 shows a sketch of the Fourier space related to a quadratic camera with the definition ranges of the Fourier components a) of the cross-correlated and autocorrelated interference signals according to the prior art and b) solely of the cross-correlated useful signal according to the present invention.

DETAILED DESCRIPTION OF THE PREFERRED EMBODIMENT

WO 2017/029160 A1 states that the imaging of the object is to be set up such that average speckle diameter D is greater than two pixel pitches P, and that furthermore the phase gradient in the camera is to be set from the interval between $2\pi/D$ and $\pi/P$. This is equivalent to the requirement on angle of incidence a of the reference beam onto the camera plane:

$$\frac{NA}{1.22*M} < \sin\alpha < \frac{\lambda_0}{2*P}$$

Here, M denotes the magnification factor of the image, i.e. the ratio of image size to object size, so that $D=M*D_0$ applies with $$D_0 = \frac{1.22*\lambda_0}{NA}$$

as the speckle size related to the object plane. On account of the random distribution of the light intensity in a speckle field, the diameter of the speckle can only be given as a statistical magnitude, which can be calculated from the autocorrelation function. For a circular aperture, an Airy function ensues (see Dainty J., "The statistics of speckle patterns", Progress in Optics, E. Wolf, ed. (Elsevier), pp. 1-46, 1977). The first zero point is usually defined as a measure for the average speckle size, which then also corresponds to the diameter of the Airy disc of the point spread function with a diffraction-limited resolution.

The right-hand side of the above inequality requires the scanability of the stripe pattern with the given camera (Nyquist condition), and the left-hand side of the inequality requires that the stripe pattern in the individual speckles must be able to be detected on the camera.

With regard to the Fourier coefficients of the cross-correlated, a stripe pattern with an amount of the wave number vector $\vec{k}_F$ in the vicinity of the Nyquist frequency is however not expedient, because then fine structures in the sought sectional areas lead to frequencies which would be located beyond the Nyquist frequency, i.e. beyond the limit of the scanability.

According to the invention, it is on the contrary advantageous rather to approach half the Nyquist frequency with $|\vec{k}_F|$ and to favourably establish the amount for the half bandwidth $\Delta k$ of the useful signal by selecting average speckle diameter D.

Speckle diameter D is limited downwards by two conditions:

(i) D must be at least as large as the fringe spacing of the stripe pattern generated by the phase gradient on the camera.

(ii) D must be so large that the bandwidth of the cross-correlated useful signal modulated with the phase gradient does not contain any frequency components beyond the Nyquist frequency of the camera.

If condition (i) is not met, it is not then possible to determine the phase positions of the speckles, and if condition (ii) is not met, useful signal information is lost.

For half bandwidth $\Delta k$ of the useful signal, condition (ii) signifies an upper limit. This can be seen from FIG. 1 $a$), in which the Fourier space of a quadratic camera is sketched. The represented circles describe the definition ranges of the non-zero Fourier coefficients of the cross-correlated signal modulated with $k_F = |\vec{k}_F|$ top left and bottom right) and of the autocorrelated signal (by k=0), wherein the circle radii are the half bandwidths of respectively $\Delta k$ and $2 \Delta k$. The circle centre points are displaced in relation to one another precisely by $|\vec{k}_F|=3 \Delta k$. In order that the definition ranges on the one hand do not overlap and on the other hand lie completely in the Fourier space of the camera, $$\Delta k \leq \frac{\sqrt{2}}{3+\sqrt{2}} \frac{\pi}{P}$$

must be selected.

If the autocorrelated interference signal is not however regarded as an interference signal at all or is simply ignored, use can be made, as sketched in FIG. 1 $b$), of a broadband up to $$\Delta k = \frac{\sqrt{2}}{1+\sqrt{2}} \frac{\pi}{P},$$

at which the Fourier components do not overlap with the complex conjugates in the definition range (except at k=0).

According to the invention, the aim is to make accessible the broadband interval $$\frac{\sqrt{2}}{3+\sqrt{2}} \frac{\pi}{P} < \Delta k = 2\pi \frac{NA}{\lambda_0} \leq \frac{\sqrt{2}}{1+\sqrt{2}} \frac{\pi}{P}$$

hitherto problematic for the image evaluation. This can be directly reformulated into a requirement on the measurement setup, namely into $$\frac{\sqrt{2}}{3+\sqrt{2}} \lambda_0 < 2NA * P \leq \frac{\sqrt{2}}{1+\sqrt{2}} \lambda_0$$

as a setup requirement for the camera parameters in relation to the wavelength used. The phase gradient can then be also selected at $$|\vec{k}_F| < 3\Delta k = 6\pi \frac{NA}{\lambda_0}.$$

In order to actually maximise the half bandwidth of the useful signal, the phase gradient should preferably be put precisely at the half Nyquist frequency. In many practical cases, however, a maximisation is not sought, but only an improvement. Other phase gradients, which are still smaller than $|\vec{k}_F|=3 \Delta k$, can then also be set by another selection of the angle of incidence of the reference light onto the camera.

It should be noted that in FIG. 1 the Nyquist frequency amounts to $$\frac{\sqrt{2}\pi}{P}$$

along the diagonal, because a quadratic camera with quadratic pixels arranged in a checker-board manner and pixel pitch P is adopted there. Along the diagonal, the effective pixel pitch is then shortened by the factor $\sqrt{2}$, i.e. there is a higher scanning density, which is known per se.

The speckle diameter on the camera must always simultaneously meet the two conditions (i) and (ii). Nothing is changed to condition (i) by the present invention. By the use of smaller phase gradients than in the prior art, condition (ii) permits greater bandwidths according to the invention and therefore smaller speckle diameters than previously. The speckle size can be reduced by a factor up to:

$$\frac{\sqrt{2}+3}{\sqrt{2}+1} = 2\sqrt{2} - 1 \approx 1.82$$

Even if speckle size D is necessarily selected intentionally somewhat larger than according to conditions (i) and (ii), in order for example to have a safety distance from the edge of the Fourier space of the camera, a markedly improved scanning of the cross-correlated is already achieved with the given camera.

Approximately three times the Fourier space can be utilised with the invention.

Three facts now have to be stated and emphasised:

I) The method of WO 2017/029160 A1 is precisely specified in a development by the present invention. In particular, greater freedom can thus be taken in the selection of the angle of incidence of the reference light onto the camera.

II) The method according to the invention gains more structural information of internal sectional areas with higher image resolution and/or enlarged image field, because it is possible to transfer to smaller speckle diameters and larger bandwidths of the useful signal than previously possible in the prior art III) The actual presence of the autocorrelated in the detected individual images is simply ignored during the actual image detection. No isolated background images (without reference) are detected, and the autocorrelated also do not have to appear the same over all the specimen depths.

It could at first be surprising to the person skilled in the art that ignoring the autocorrelated would be possible without harm.

The invention relates from the outset to a sequence of camera images which is obtained by changing the path length of the reference light in the manner of a Time-Domain-OCT. Not a single one of these images is accessible to direct filtering to separate background and useful signal. But in the combined view of the images indexed with the path length, it appears that a numerical averaging procedure according to the invention virtually erases the useful signal in a mean value image. A still strongly structured image of the mean values then remains, which is independent of the reference light and as such can be perceived as a background image. This background image essentially comprises the autocorrelated for the specimen depth, from the surrounding area of which the path length interval is selected for averaging the indexed individual images, and furthermore also all the static structures from the instrumental set-up, e.g. dust particles on lenses and suchlike.

It is clear that a path length interval can be defined for each individual image detected and indexed with path length $l_0$ of the reference light. A distinction can be made between two cases:

If the path lengths of the interval differ at most by coherence length $l_c$ of the light, e.g.

$$\left[l_0 - \frac{l_c}{2}, l_0 + \frac{l_c}{2},\right]$$

the individual images comprise speckles in respect of indexes from this interval, which change from constructive into destructive interference with a variation of the path length of the reference light by $\lambda_0/2$. If the reference mirror is displaced with a technical drive by several wavelengths between two individual images, the brightness of these speckles is virtually a random magnitude distributed around 0.5. If a plurality of such images are added, all the speckles assume on average the same value of 0.5, and the structure of the useful signal becomes invisible. The Fourier coefficients of the cross-correlated become—with the exception of the integral, i.e. of the coefficient k=0—zero.

For the measurement of larger specimen volumes, however, it may be more favourable to carry out only two or fewer measurements per coherence length in order to reduce the measurement time. Since the measurements in this case no longer originate from the same coherence volume, the speckle patterns in the cross-correlated are usually no longer correlated in the case of measurements in scattering fabric. Here, therefore, the phases and also the spatial positions of the speckles are randomly distributed. In this case, too, the cross-correlated can be erased by averaging over a none too large number of images—typically up to 20 images.

A path length interval of the form $[l_0-\Delta l, l_0+\Delta l,]$ should be designated as a surrounding interval of path length of $l_0$. A partial number of detected camera images is assigned to the surrounding interval. The partial number can also be denoted as a stack of individual images. If these are for example images at the path lengths $l_j \in [l_0-\Delta l, l_0+\Delta l]$, $j=1, \ldots, N$, a weighted stack mean value reads $$B_{av}(x, y, l_0) = \frac{1}{N}\sum_{j=1}^{N}[B(x, y, l_j) - B_0(l_j)] \times G(l_j)$$

wherein x, y denote pixel coordinates and $B_{av}$, $B$, $B_0 \in [0,1]$ denote brightness values (or grey scale values) on the pixels. Parameter $B_0$ can be used to standardise the average brightness of all the individual images if this appears necessary. Parameter G Can be used as a weighting factor once again if required to standardise the contrast breadth of the images of the stack. They are in addition suitable for leaving out of account individual—e.g. obviously erroneous—images and/or for limiting the effective range of the summation, e.g. by diminishing weights with the distance to $l_0$.

Ultimately, the user will, in view of a detected sequence of camera images, determine in post-processing the precise selection of the parameters of the stack averaging. The determination of the parameters can also be automated, in particular can be carried out with software on a conventional computer, if the properties of the image detection device are known to the user and he specifies specific requirements on the background images. An illustrative criterion to the effect that the calculated stack mean value represents a good approximation for a background image independently of the reference arm length is its slow variability of all the image components in the transition from $l_0$ to a nearby depth plane, i.e. the following should hold $B_{av}(x, y, l_0) \approx B_{av}(x,y,l_0+dl)$.

After the determination of the background images for all the detected camera images, the differences $$B'(x,y,l_0)=B(x,y,l_0)-B_{av}(x,y,l_0)$$

can be calculated in the simplest and preferred case and the structurally improved images B' can be further processed. It is expedient to then subject the structurally improved images to a Fourier transformation and to eliminate any remaining coefficients close to k=0 and the complex conjugates (Fourier filtering). The Fourier reverse transformation then leads to an image of an inner sectional area of the illuminated object indexed with the path length displacement $l_0$ of the reference light, i.e. the sectional area can be assigned to a depth position in the object.

It is thus possible, with the method according to the invention for the illumination of inner sectional areas of scattering objects, which relates specifically to a sequence of camera images at different path lengths of the reference light and observes the condition according to the invention for the illumination parameters, to arrive at a dataset, which in post-processing generates sectional images with a higher resolution and larger image field than in the prior art. This post-processing is optionally chronologically downstream of the data acquisition within the scope of the disclosure of WO 2017/029160 A1, it can even take place not until very much later by a third party and to this extent does not have to be an integral component of the illumination method according to the invention or of a measurement device. The generation of the raw dataset is itself also a valuable achievement in its own right, the usefulness of which is not in doubt according to the above explanations.

The previously described invention is preferably used for the illumination of biological scattering specimens, particularly preferably living tissue, very particularly preferably the illumination of the retina of a living eye. Apart from the medical applications in ophthalmology, the invention can also preferably be used by a user for the biometric verification of the identity of the user.

The invention claimed is:

1. A method for illuminating a sequence of sectional areas in the interior of a light-scattering object, the method comprising:
   provision of a light source, which emits light with a predetermined central wavelength $\lambda_0$ and a coherence length less than 25 microns;
   splitting the light of the light source into specimen light and reference light;
   illumination of the object over the surface with the specimen light;
   imaging of the specimen light scattered by the object with numerical aperture NA and magnification factor M onto an electronic camera with pixels with a pitch P along at least one axis in the camera plane;
   causing interference of reference light and specimen light on the camera by establishing a path length profile and a phase gradient of the reference light along the predetermined axis in the camera plane;
   displacement of the path length profile of the reference light at a time-dependent rate; and
   detection of further camera images in each case at least indexed with a dimension for the time-dependent displacement of the path length profile, wherein the condition $$\frac{\sqrt{2}}{3+\sqrt{2}}\lambda_0 < \frac{2NA*P}{M} \leq \frac{\sqrt{2}}{1+\sqrt{2}}\lambda_0$$

is met.

2. The method according to claim 1, wherein the phase gradient along the predetermined axis in the camera plane is established on half the Nyquist frequency.

3. The method according to any one of the preceding claims, wherein a surrounding interval of the indexing is predetermined for each indexed camera image of at least a partial number of the detected camera images and a weighted stack mean value of all the camera images of the surrounding interval is calculated and the calculated stack mean value of the indexed camera image is deducted to calculate the structurally improved camera image.

4. The method according to claim 3, further comprising calculation of the images of the sectional areas in the interior of the object by two-dimensional Fourier filtering of the structurally improved camera images.

5. The method according to claim 1, wherein the light-scattering object is the retina of a living eye.

6. The method according to claim 5, further comprising biometric verification of the identity of a user.

* * * * *